(12) United States Patent
Isola et al.

(10) Patent No.: US 11,291,863 B2
(45) Date of Patent: Apr. 5, 2022

(54) POSITIONING ASSISTANCE DEVICE FOR FOCAL RADIATION THERAPY

(71) Applicant: KONINKLIJKE PHILIPS N.V., Eindhoven (NL)

(72) Inventors: Alfonso Agatino Isola, Eindhoven (NL); Guillaume Leopold Theodorus Frederik Hautvast, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 282 days.

(21) Appl. No.: 16/469,680

(22) PCT Filed: Dec. 12, 2017

(86) PCT No.: PCT/EP2017/082491
§ 371 (c)(1),
(2) Date: Jun. 14, 2019

(87) PCT Pub. No.: WO2018/108952
PCT Pub. Date: Jun. 21, 2018

(65) Prior Publication Data
US 2020/0009403 A1   Jan. 9, 2020

(30) Foreign Application Priority Data

Dec. 16, 2016   (EP) .................................. 16204563

(51) Int. Cl.
*A61N 5/10*   (2006.01)

(52) U.S. Cl.
CPC .......... *A61N 5/1049* (2013.01); *A61N 5/1007* (2013.01); *A61N 5/1071* (2013.01); *A61N 5/1039* (2013.01); *A61N 2005/1055* (2013.01); *A61N 2005/1058* (2013.01)

(58) Field of Classification Search
CPC .......... A61N 5/1001–1029; A61N 5/103–1039
See application file for complete search history.

(56) References Cited

U.S. PATENT DOCUMENTS

| 2003/0065260 A1* | 4/2003 | Cheng .................. A61B 8/0833 600/427 |
| 2013/0102831 A1 | 4/2013 | Kindlein et al. |

OTHER PUBLICATIONS

Battisti et al "Adaptive Planning Strategy for High Dose Prostate Brachytherapy . . ." Phys. Med. Biol. 61, pp. 2177-2195 (2016).
(Continued)

*Primary Examiner* — Thaddeus B Cox
(74) *Attorney, Agent, or Firm* — Sherry Austin

(57) ABSTRACT

An efficient direct parameter optimization (DPO) approach is provided, in which a dosimetry gradient-based iterative greedy technique is applied to determine positioning assistance information for catheter insertion in focal radiation therapy, by toggling between optimization of candidate catheter positions and candidate radiation source dwelling times. In the specific case of free hand delivered catheters, the insertion point may be directly selected by the human expert. Using monitoring of the catheter position by additional imaging modalities such as magnetic resonance imaging or ultrasound imaging, the method enables real-time orientation guidance and adaptive dose correction in the course of treatment delivery.

11 Claims, 5 Drawing Sheets

(56) References Cited

OTHER PUBLICATIONS

Cunha et al "Toward Adaptive Stereotactic Robotic Brachytheraphy for Prostate Cancer . . . " Minim, Invasive Ther. Applied Technol. 19(4) p. 189-202 (2010).
Battisti et al "An Automated Optimization Tool for High-Dose Rate (HDR) Prostate Brachytheray . . . " Phys. Med. Biol. 60, pp. 7567-7583 (2015).
E. Lessard et al., "Inverse planning anatomy-based dose optimization for HDR-brachytherapy of the prostate using fast simulated annealing algorithm and dedicated objective function", Med. Phys. (2001), vol. 28(5), pp. 773-779.
Search Report From PCT/EP2017/082491 dated Mar. 14, 2018.
Nocedal, J., Wright, S. "Numerical Optimization", 1999, Springer, Berlin.

* cited by examiner

POSITIONING ASSISTANCE DEVICE FOR FOCAL RADIATION THERAPY

CROSS REFERENCE TO RELATED APPLICATIONS

This application is a U.S. national phase application of International Application No. PCT/EP2017/082491 filed on Dec. 12, 2017, which claims the benefit of EP Application Serial No. 16204563.7 filed on Dec. 16, 2016 and is incorporated herein by reference.

FIELD OF THE INVENTION

The present invention is in the field of focal radiation therapy, such as high intensity focused ultrasound (HIFU) ablation, radio frequency (RF) ablation, microwave ablation, laser ablation or High Dose Rate (HDR) brachytherapy. More specifically, it relates to a device and a method for assisting in positioning of catheters in a focal radiation therapy with respect to a pre-determined target volume and a given catheter insertion point.

BACKGROUND OF THE INVENTION

Focal radiation therapy, such as high intensity focused ultrasound (HIFU) ablation, radio frequency (RF) ablation, microwave ablation, laser ablation or High Dose Rate (HDR) brachytherapy, etc. has shown to be a method of choice to treat tumors in different organs. In focal therapy of the prostate, brachytherapy is used to treat the tumor only, while sparing surrounding tissues. Compared to traditional whole gland brachytherapy, focal brachytherapy is aimed to be equally effective, while reducing therapy side effects.

For example, HDR brachytherapy has proven to have an excellent survival and local control rate and very limited side effects for the patient. In particular, HDR brachytherapy has shown to be a method of choice to treat prostate and breast cancers. To determine the ideal HDR dwell positions and dwell times, so-called inverse planning methods are used for determining a treatment. Based on a determination of a target volume and of critical organs, target doses as well as constraints with respect to organs at risk and importance factors for each are given. An optimization is then performed to find the treatment plan which best matches all the input criteria, thus optimizing a radiation dose, considering objectives for the target volume, as well as the constraints, which are usually expressed as a set of linear relations forming a linear system that is to be solved.

The publication "Adaptive planning strategy for high dose prostate brachytherapy-a simulation study on needle positioning errors", M Battisti et al., 2016, Phys. Med. Biol. 61, pp 2177-2195 describes dose plan adaptation strategy for HDR prostate brachytherapy with feedback on the needle position. A dose plan is made at the beginning of the interventional procedure and updated after each needle insertion in order to compensate for possible needle positioning errors.

A similar approach is described in the publication "Toward adaptive stereotactic robotic brachytherapy for prostate cancer: Demonstration of an adaptive workflow incorporating inverse planning and an MR stealth robot", J Cunha et al., Minim Invasive Ther Allied Technol., 2010, 19(4), pp 189-202. Inverse planning is used to generate a seed placement plan, and coordinates for ten needles and 29 seeds are transferred to a robot. After every two needles placed, an image is acquired. The placed seeds are identified and validated prior to placing the seeds in the next two needles. Prior to seed deposition an adjustment is determined if the needle catheter is in the wrong position.

The publication "An automated optimization tool for high-dose-rate (HDR) prostate brachytherapy with divergent needle pattern", M Battisti et al., 2015, Phys. Med. Biol. 60, pp 7567-7583 describes an automatic inverse dose planning optimization tool for focal HDR prostate brachytherapy with needle insertions in a divergent configuration. A complete optimizer workflow is proposed which includes the determination of (1) the position of the center of rotation, (2) the needle angulations and (3) the dwell times.

US 2013/0102831 A1 relates to a real time radiation treatment planning system for use in effecting radiation therapy of a preselected anatomical portion of an animal body using hollow needles. According to embodiments of the invention, the system may include a processing means configured to perform a three-dimensional imaging algorithm and a three-dimensional image segmentation algorithm, with respect to one or more specific organs within the pre-selected anatomical portion and with respect to the needles, for converting the image data obtained with an imaging means into a three-dimensional image of the anatomical portion, using at least one single or multi-objective anatomy-based genetic optimization algorithm. For pre-planning or virtual simulation purposes, the processing means is arranged to determine in real time the optimal number and position of at least one of the needles, positions of energy emitting sources within the needles, and the dwell times of the energy emitting sources at the positions. For post-planning purposes, the processing means is arranged to determine, based on three-dimensional image information, in real time the real needle positions and the dwell times of the energy emitting sources for the positions.

SUMMARY OF THE INVENTION

It would be desirable to provide positioning assistance for grid-less catheter insertion techniques executing catheter insertion via human free hand and/or robotic arms in a plan-less, freehand placement of catheters to deliver a better conformed dose distribution in difficult cases where a tumor is not optimally positioned with respect to a therapy template.

According to a first aspect of the present invention, a positioning assistance device for assisting in positioning of catheters in a focal radiation therapy with respect to a pre-determined target volume and a given catheter insertion point is provided. The positioning assistance device comprises:

a candidate catheter providing unit, which is configured to provide candidate catheter data associated with the given catheter insertion point and defining candidate catheters by a respective candidate inserted-catheter position, respective candidate dwelling positions of radiation sources inside a given candidate catheter, and respective associated candidate dwelling times;

a catheter pre-selection unit, which is configured to
  ascertain and provide a gradient with respect to dwelling time of a composite constraint function for each current candidate catheter, using the current candidate dwelling times at associated current candidate dwelling positions of the candidate catheter, the composite constraint function combining at least two linear constraints representing clinical objectives with respect to radiation dose governing the focal radiation therapy; and to pre-select a predetermined number of one or more candidate catheters from the candidate catheters, which are associated with a steepest descent value of the gradient among the candidate catheters;

a dwelling-time pre-selection unit, which is configured to ascertain and pre-select, using the current pre-selected candidate catheters, those current candidate dwelling times for the respective candidate dwelling positions, which achieve a minimum of a scalar composite constraint function of dwelling time combining the at least two linear constraints; and a positioning assistance control unit, which is configured to alternatingly drive operation of the catheter pre-selection unit and the dwelling-time pre-selection unit over a plurality of iteration cycles, and to provide, upon detecting that in a current iteration cycle the catheter pre-selection unit has provided a non-negative value of the gradient of the composite constraint function for at least one of the candidate catheters, an output indicative of a next target catheter position as that of the at least one current pre-selected candidate catheter.

The positioning assistance device of the first aspect of the present invention achieves positioning assistance in the form of a catheter positioning optimization (CPO) in combination with a dwelling time optimization (DTO) in grid-less free hand focal radiation therapy. It performs a direct parameter optimization (DPO) for providing positioning assistance information by iteratively toggling between CPO and DTO and thus determines the best set of catheter positions and corresponding dwelling times satisfying all clinical goals.

The positioning assistance device does not need an initial plan to start from. As such the positioning assistance device assists in a plan-less, freehand placement of catheters, in which adaptation also occurs before actually placing the individual catheters. When the needle is at the skin of a patient or just enters the patient, the positioning assistance device can propose an optimum position and guide the user to insert under an angle that has the best impact on the dose to be delivered. When inserting a second needle, be it at the same insertion point or in another insertion point, it can again indicate the best needle angulation and positioning.

Thus, positioning assistance including orientation guidance and adaptive dose correction in the course of focal radiation therapy delivery are made possible. Every time a catheter is positioned by the surgeon or by a robotic arm, any tracked misplacements can be taken into account to adaptively re-optimize the remaining set of catheters and corresponding dwell times in order to recover dose accuracy, homogeneity and conformality. Given the compact and elegant nature of its technical concept, the proposed positioning assistance device ensures that efficient and accurate plans will be implemented for a prescribed clinical protocol, while reducing the workload for medical experts involved in an inverse planning process and catheter insertion.

In the following, embodiments of the positioning assistance device of the present invention will be described.

The positioning assistance device is preferably implemented for assistance in real-time, which is supported by additional features provided in the context of preferred embodiments described herein below.

For assisting in the positioning during insertion of additional catheters, in one embodiment, the catheter pre-selection unit is additionally configured to receive inserted catheter data, which is associated with all catheters already inserted into the target volume and which is indicative of respective inserted-catheter positions, respective dwelling positions of radiation sources, and respective dwelling times associated with the dwelling positions of the catheters already inserted;

determine a current radiation dose value associated with the dwelling positions and dwelling times associated with the catheters already inserted; and to determine, for the given candidate catheter, the gradient of the composite constraint function additionally using the current radiation dose value associated with the catheters already inserted.

Real-time operation is preferably supported in this embodiment of the positioning assistance device by the catheter pre-selection unit being additionally configured to receive three-dimensional image data of the target volume to be exposed to the radiation and of one or more catheters currently inserted into the target volume, and to determine the catheter data of catheters currently inserted from the image data.

A particularly advantageous handling of misplaced catheters in the context of the positioning assistance device is achieved in embodiments, wherein the catheter pre-selection unit is additionally configured, upon detecting a misplaced catheter already inserted into the target volume by detecting a difference between the positioned catheter data determined from the image data and the associated target catheter position previously provided for this catheter as an output by the positioning assistance control unit, to add the misplaced catheter to the candidate catheters, and wherein the positioning assistance control unit is additionally configured to determine and provide adapted dwelling position information and adapted dwelling-time information for the misplaced catheter.

In the case of divergent catheter positioning in preferred embodiments of the positioning assistance device the catheter pre-selection unit is configured to calculate the gradient with respect to dwelling time of the composite constraint function for each current candidate catheter as:

$$g_c = \sum_{j=1}^{N_c^t} \begin{cases} \frac{\partial F(t)}{\partial t_{c,j}}, & \text{if } \frac{\partial F(t)}{\partial t_{c,j}} < 0 \\ 0, & \text{otherwise} \end{cases}, c = 1, \ldots, N_{cat}^{r^*}. \quad (1)$$

wherein $g_c$ is the gradient with respect to dwelling time of the composite constraint function for a respective current candidate catheter c is an index identifying a respective catheter, $N_c^t$ is a total number of dwelling positions for the c-th catheter, t is dwelling time vector of dwelling times at dwelling positions, j is an index identifying a respective dwell time position, $r^*$, is an index identifying a current insertion point, $N_{cat}^{r^*}$ is the total number of divergent catheters passing the current insertion point, $$F(t) = \sum_{i=1}^{m} w_i f_i(t),$$

i is an index identifying a respective linear constraint, m is a total number of linear constraints, $f_i(t)$ is a set of linear constraints representing clinical objectives given as functions of dwelling times t of a respective radiation source in the respective catheter, and $w_i$ are weighting factors indicative of a priority of a given linear constraint.

In this embodiment, the dwelling-time pre-selection unit is preferably configured to ascertain the current candidate dwelling times for the respective candidate dwelling positions, which achieve a minimum of the scalar composite constraint function $$F(t) = \sum_{i=1}^{m} w_i f_i(t), \qquad (2)$$

taking into account predetermined upper and lower limits for the dwelling time.

In embodiments extending this concept to the case where at least one catheter is already inserted, the candidate pre-selection unit is suitably additionally configured to determine for the given candidate catheter, the gradient of the composite constraint function additionally using the current radiation dose associated with the catheters already inserted as (equation (3)):

$$g_c = \sum_{j=1}^{N_c^t} \begin{cases} \frac{\partial F(M_0 t_0 + M_1 t_1 + \ldots + M_n t_n)}{\partial t_{c,j}}, & \text{if} \\ \frac{\partial F(M_0 t_0 + M_1 t_1 + \ldots + M_n t_n)}{\partial t_{c,j}} < 0 \\ 0, & \text{otherwise,} \end{cases}$$

$$c = 1, \ldots, N_{cat}^{r^*}.$$

wherein $M_0, M_1, \ldots M_n$ are dose rate influence matrices of catheters of index n=0,1, . . . , n which are already inserted, $t_0, t_1, \ldots t_n$ are dwelling times associated with the catheters of index n=0,1, . . . , n which are already inserted.

In such embodiments, the dwelling-time pre-selection unit is preferably configured to ascertain the current candidate dwelling times for the respective candidate dwelling positions, which achieve a minimum of the scalar composite constraint function $$F(t) = \sum_{i=1}^{m} w_i f_i(t) = \sum_{i=1}^{m} w_i f_i (M_0 t_0 + M_1 t_1 + \ldots + M_n t_n), \qquad (4)$$

and provide these as an output.

The positioning assistance device is in some embodiment provided with additional functionality for assisting in the selection a set of candidate insertion points. In such embodiments, the positioning assistance device further comprises a candidate insertion point providing unit, which is configured to provide candidate insertion point data associated with the given target volume and defining candidate insertion points by a respective candidate insertion point position; and an insertion point selection unit, which is configured to
 request and receive, for each candidate insertion point, a respective set of candidate catheters from the candidate catheter providing unit;
 ascertain and provide for each candidate insertion point a sum over all candidate catheters of the gradients with respect to dwelling time of the composite constraint functions, using the candidate insertion point data and the candidate catheter data; and to
 select as the next insertion point from the candidate insertion points that candidate insertion point, which among the candidate insertion points is associated with the steepest descent value of the sum over all candidate catheters of the gradients.

For assisting in real-time operation in these embodiments of the positioning assistance device, the candidate insertion point providing unit is preferably additionally configured to receive three-dimensional image data of the target volume to be exposed to the radiation;

determine a two-dimensional axial projection of the target volume onto a predetermined projection plane on or in a subject;

determine a geometrical center of mass of the axial projection of the target volume;

determine the candidate insertion points as grid points of a pre-determined two-dimensional grid having the center of mass as a center point.

The positioning assistance device can be provided as a separate add-on device to extend and enhance the functionality of an existing focal radiation therapy arrangement already in use. It can otherwise be provided as an integral part of a focal radiation therapy arrangement. In any case, a focal radiation therapy arrangement implementing the present invention comprises at least an imaging device configured to provide three-dimensional image data of a target volume to be exposed to the radiation and of one or more catheters currently inserted into the target volume;

a catheter positioning assistance device according to the first aspect of the invention or one of its embodiments, which is configured to receive the image data and to provide the next target catheter position in a form registered with respect to the image data.

Some embodiments of the focal radiation therapy arrangement further comprise a catheter insertion robot, which is configured to receive the target insertion point and the target catheter position from the positioning assistance device, and to insert a catheter into a subject using the received target insertion point and the target catheter position.

According to a second aspect of the invention, a positioning assistance method for assisting in positioning of catheters in a focal radiation therapy with respect to a pre-determined target volume and a given catheter insertion point is provided. The positioning assistance method comprises:

a candidate catheter providing stage, comprising providing candidate catheter data associated with the given catheter insertion point and defining candidate catheters by a respective candidate inserted-catheter position, respective candidate dwelling positions of radiation sources inside a given candidate catheter, and respective associated candidate dwelling times;

a catheter pre-selection stage, comprising
 ascertaining and providing a gradient with respect to dwelling time of a composite constraint function for each current candidate catheter, using the current candidate dwelling times at associated current candidate dwelling positions of the candidate catheter, the composite constraint function combining at least two linear constraints representing clinical objectives with respect to radiation dose governing the focal radiation therapy; and
 pre-selecting a predetermined number of one or more candidate catheters from the candidate catheters, which are associated with a steepest descent value of the gradient among the candidate catheters;
a dwelling-time pre-selection stage, comprising
ascertaining and pre-selecting, using the current pre-selected candidate catheters, those current candidate dwelling times for the respective candidate dwelling positions, which achieve a minimum of a scalar composite constraint function of dwelling time combining the at least two linear constraints; and
a positioning assistance controlling stage, comprising alternatingly driving operation of the catheter pre-selection stage and the dwelling-time pre-selection stage over a plurality of iteration cycles, and providing, upon detecting that in a current iteration cycle the catheter pre-selection unit has provided a non-negative value of the gradient of the composite constraint function for at least one of the candidate catheters, an output indicative a next target catheter position as that of the at least one current pre-selected candidate catheter.

The positioning assistance method of the second aspect shares the advantages of the positioning assistance device of the first aspect of the invention. It is particularly suited for automated processing, be it in the form an implementation of executable software on programmable processor hardware, or in the form of execution by application specific integrated circuitry.

According to a third aspect of the present invention, a computer program is provided comprising executable code for executing the method of claim of the third aspect or one of its embodiment when executed by a processor of a computer.

It shall be understood that the positioning assistance method of claim 1, and the computer readable medium of claim 2 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
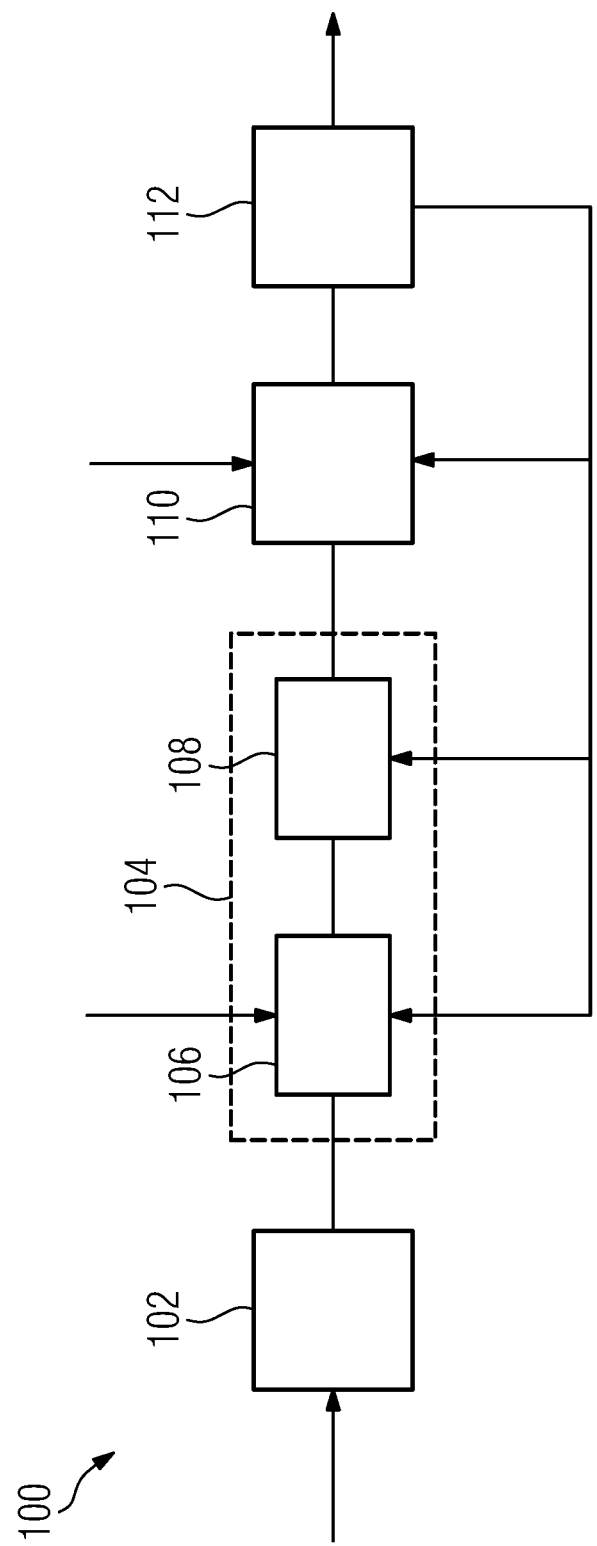
FIG. 1 is a schematic block diagram of an embodiment of a positioning assistance device for assisting in positioning of catheters in a focal radiation therapy with respect to a pre-determined target volume and a given catheter insertion point.

FIG. 1 is a schematic block diagram of a positioning assistance device 100 for assisting in positioning of catheters in a focal radiation therapy with respect to a pre-determined target volume and a given catheter insertion point, in accordance with an embodiment of the present invention.

Focal radiation therapy is used to treat a tumor only, while sparing surrounding tissue. Compared to traditional whole gland approaches in radiation therapy, focal radiation therapy, such as for example focal brachytherapy, is aimed to be equally effective while reducing therapy side effects. The present embodiment of a positioning assistance device 100 is designed in particular for application in grid-less adaptive focal radiation therapy, where human free hand, a robotic arm or a combination of both is used to implant catheters and deliver dose at different dwelling positions.

The positioning assistance device 100 has a candidate catheter providing unit 102. The candidate catheter providing unit is configured to provide candidate catheter data. The candidate catheter data defines candidate catheters by a respective candidate inserted-catheter position, respective candidate dwelling positions of radiation sources inside a given candidate catheter, and respective associated candidate dwelling times. The candidate inserted-catheter position defines a candidate target position of a catheter after insertion. It suitably describes this potential inserted-catheter position in terms of a given coordinate system that also serves for describing a position and extension of a target volume to be treated by the focal radiation therapy. The target volume typically describes the position and extension of a tumor to be treated. The candidate dwelling positions of radiation sources inside a given candidate catheter describe candidate locations of predetermined radiation sources (such as radioactive seeds) inside the subject catheter. The dwelling positions are suitable defined in terms of the same coordinate system as the candidate inserted-catheter position and the target volume. The candidate dwelling times are associated with the respective radiation sources and define a potential limited time span of radiation treatment of the target volume with the respective radiation source.

Such candidate catheter data is associated with a given catheter insertion point. This catheter insertion point forms an input to the candidate catheter providing unit and is thus taken as a given in the present embodiment. The catheter insertion point can be set by free-hand human control and is provided to the candidate catheter providing unit as catheter insertion point data in terms of the mentioned coordinate system using known technical solutions such as a suitable imaging modality for monitoring the current position of catheters in a focal radiation therapy arrangement, in combination with a registration unit (not shown in FIG. 1).

The candidate catheter providing unit provides candidate catheter data defining a plurality of candidate catheters, of which only a predetermined number are to be selected by the positioning assistance device 100. The number of catheters to be selected can be pre-set globally or individually in each catheter selection step by manual input. The catheter selection involves a pre-selection which is performed by a catheter pre-selection unit 104. The candidate catheter data of each of the current candidate catheters is fed into a gradient evaluation unit 106 of the catheter pre-selection unit 104.

The gradient evaluation unit 106 is pre-programmed by prior input with a composite constraint function. The composite constraint function combines at least two linear constraints representing clinical objectives with respect to radiation dose governing the focal radiation therapy for a given patient. In other words, these linear constraints represent clinical objectives for the target volume, as well as for organs at risk in the process of focal radiation therapy. The linear constraints are defined and provided as an input by a planner who takes care to translate the prescribed clinical protocol, i.e., the given list of prescribed clinical goals, to corresponding dose-based mathematical objective functions, which, e.g., form convex quadratic functions. Generally, clinical goals for all regions of interest, i.e., tumor and organs at risk, are translated into corresponding two- or one-sided closed proper convex quadratic functions of class $C^2$. For example, they form minimum, maximum and uniform dose constraints. Very common is also the use of dose volume histogram (DVH) clinical objectives. Here, the minimum, maximum and uniform dose objectives previously exposed can be enforced only over a fraction of the volume of the region of interest.

A set of a number m of linear constraints representing clinical objectives can be represented mathematically as functions of a dose voxel vector d in the form $$f_1(d), \ldots, f_m(d) : \mathbb{R}^n \to \mathbb{R}$$

wherein n describes the number of dose voxel positions.

In the gradient evaluation unit 106, this set of linear constraints is pre-programmed prior to operation in transformed form as linear constraints in terms of dwelling times t of the radiation source in the catheters at the respective dwelling positions, by enforcing the well-known dose linear map d=Mt, where M is the well-known dose rate influence matrix. For the sake of readability, in this specification, the matrix M is neglected in many formulas, and only explicitly exposed where needed.

The gradient evaluation unit 106 is configured to ascertain and provide as an output a gradient value with respect to dwelling time of a composite constraint function, using the current candidate dwelling times at associated current candidate dwelling positions of the candidate catheter. In the present embodiment, the gradient evaluation unit 106 is configured to calculate the gradient value $g_c$ with respect to dwelling time of the composite constraint function for each current candidate catheter as (equation (1)):

$$g_c = \sum_{j=1}^{N_c^t} \begin{cases} \frac{\partial F(t)}{\partial t_{c,j}}, & \text{if } \frac{\partial F(t)}{\partial t_{c,j}} < 0 \\ 0, & \text{otherwise} \end{cases}, c = 1, \ldots, N_{cat}^{r^*}.$$

wherein c is an index identifying a respective catheter, $N_c^t$ is a total number of dwelling positions for the c-th catheter, t is a dwelling time vector of dwelling times at dwelling positions, j is an index identifying a respective dwell time position, r*, is an index identifying a current insertion point, $N_{cat}^{r^*}$ is the total number of catheters passing the current insertion point, $$F(t) = \sum_{i=1}^{m} w_i f_i(t),$$

i is an index identifying a respective linear constraint, m is a total number of linear constraints, $f_i(t)$ is a set of linear constraints representing clinical objectives given as functions of dwelling times t of a respective radiation source in the respective catheter, and $w_i$ are weighting factors indicative of a priority of a given linear constraint. The weighting factors are typically provided as an output of radiation therapy planning for the given patient and are pre-programmed, as are the linear constraints.

The catheter pre-selection unit 104 further has a pre-selection control unit 108, which is configured to pre-select a predetermined number of one or more candidate catheters from the candidate catheters, namely that or those, which are associated with one or more steepest descent values of the gradient among the candidate catheters. In other words, those candidate catheters, which have the most negative gradient values determined by the gradient evaluation unit 106, are pre-selected by the pre-selection control unit.

In the case where at least one catheter is already inserted, the gradient evaluation unit 106 of the candidate pre-selection unit 104 determines, for the given candidate catheter, the gradient of the composite constraint function in a different way. It additionally receives inserted catheter data, which is associated with all catheters already inserted into the target volume and which is indicative of respective inserted-catheter positions, respective dwelling positions of radiation sources, and respective dwelling times associated with the dwelling positions of the catheters already inserted. It determines a current radiation dose value associated with the dwelling positions and dwelling times associated with the catheters already inserted. It further determines, for the given candidate catheter, the gradient of the composite constraint function additionally using the current radiation dose value associated with the catheters already inserted. Specifically, the gradient value is in this case determined as (equation (3))

$$g_c = \sum_{j=1}^{N_c^t} \begin{cases} \frac{\partial F(M_0 t_0 + M_1 t_1 + \ldots + M_n t_n)}{\partial t_{c,j}}, & \text{if} \\ \frac{\partial F(M_0 t_0 + M_1 t_1 + \ldots + M_n t_n)}{\partial t_{c,j}} < 0 \\ 0, & \text{otherwise,} \end{cases}$$

$$c = 1, \ldots, N_{cat}^{r^*}.$$

wherein $M_0, M_1, \ldots M_n$ are dose rate influence matrices of catheters of index n=0,1, ..., n which are already inserted, $t_0, t_1, \ldots, t_n$ are dwelling times associated with the catheters of index n=0,1, ..., n which are already inserted.

The pre-selected candidate catheter(s) form an intermediate output of the catheters positioning optimization (CPO).

The positioning assistance device 100, however, goes further in evaluation before providing positioning assistance output. It additionally takes into account a dwelling times optimization (DTO) to find the best candidate catheter. The pre-selected candidate catheter data are thus provided by the catheter pre-selection unit 104 as an input to a dwelling-time pre-selection unit 110.

The dwelling-time pre-selection unit 110 is configured to ascertain and pre-select, using the current pre-selected candidate catheters, those current candidate dwelling times for the respective candidate dwelling positions, which achieve a minimum of a scalar composite constraint function of dwelling time combining the at least two linear constraints. In the present embodiment, the dwelling-time pre-selection unit 110 is configured to ascertain the current candidate dwelling times for the respective candidate dwelling positions, which achieve a minimum of the scalar composite constraint function (equation (2)):

$$F(t) = \sum_{i=1}^{m} w_i f_i(t),$$

taking into account predetermined upper and lower limits for the dwelling time, which are provided as input parameters. In case at least one catheter is already inserted, the dwelling-time pre-selection unit ascertains the current candidate dwelling times for the respective candidate dwelling positions in a different way, namely by identifying those candidate dwelling times which achieve a minimum of the scalar composite constraint function (equation (4))

$$F(T)\Sigma_{i=1}^{m} w_i f_i(t) = \Sigma_{i=1}^{m} w_i f_i(M_0 t_0 + M_1 t_1 + \ldots + M_n t_n).$$

thus also taking into account the dose rate influence matrices of catheters of index n=0,1, . . . , n which are already inserted.

A positioning assistance control unit 112 receives the currently determined gradient value of the composite constraint function for the at least one of the pre-selected candidate catheters, as determined by the catheter pre-selection unit. It checks whether the catheter pre-selection unit 104 has provided a non-negative value of the gradient of the composite constraint function for the one or more candidate catheters. If this is not the case, the positioning assistance control unit 112 triggers a next iteration cycle of the catheters positioning optimization (CPO) by the catheter pre-selection unit 104, and subsequent dwelling times optimization (DTO) by the dwelling-time pre-selection unit 110. Only upon detecting that in a current iteration cycle the catheter pre-selection unit 104 has provided a non-negative value of the gradient of the composite constraint function for at least one of the candidate catheters, a positioning assistance output indicative of a next target catheter position as that of the at least one current pre-selected candidate catheter is provided. Otherwise, the positioning assistance control unit 112 alternatingly drives operation of the catheter pre-selection unit 104 and the dwelling-time pre-selection unit 110 over a plurality of iteration cycles.

This iterative process can be repeated for determining a next catheter to be placed. It is stopped as soon as the desired maximum number of catheters will be reached, and/or as soon as the planner's prescribed dose-based quality is achieved.

In some embodiments, only one candidate catheter is pre-selected by the pre-selection unit and thus positioning assistance for only one catheter is eventually provided by the positioning assistance device 100. To reduce total computation expenditure, other embodiments pre-select more than one new catheter position per run. This reduces the number of iteration cycles needed to find the best solution, to the expense of some degradations in terms of dose accuracy.

Thus, the positioning assistance device 100 determines a set of procedure parameters in terms of catheter positioning and dwelling time that has been optimized in an iterative manner, toggling between optimization of candidate catheter positions and radiation source dwelling times. The candidate catheter pre-selection unit 104 keeps dwelling times fixed and pre-selects the most suitable candidate catheter according to the steepest gradient descent criterion. Then, one or more pre-selected catheter positions are kept fixed and the most suitable dwelling times are pre-selected, and so on, until the at least one current pre-selected catheter achieves a non-negative value of the gradient of the composite constraint function.

Candidate catheter data and associated dwelling times can be initialized by exploiting a-priori knowledge. If no such initialization is available, a completely empty initial setting is used. The described iterative strategy assists in positioning catheter by catheter and thus populates the set of catheters used.

Figure 2:
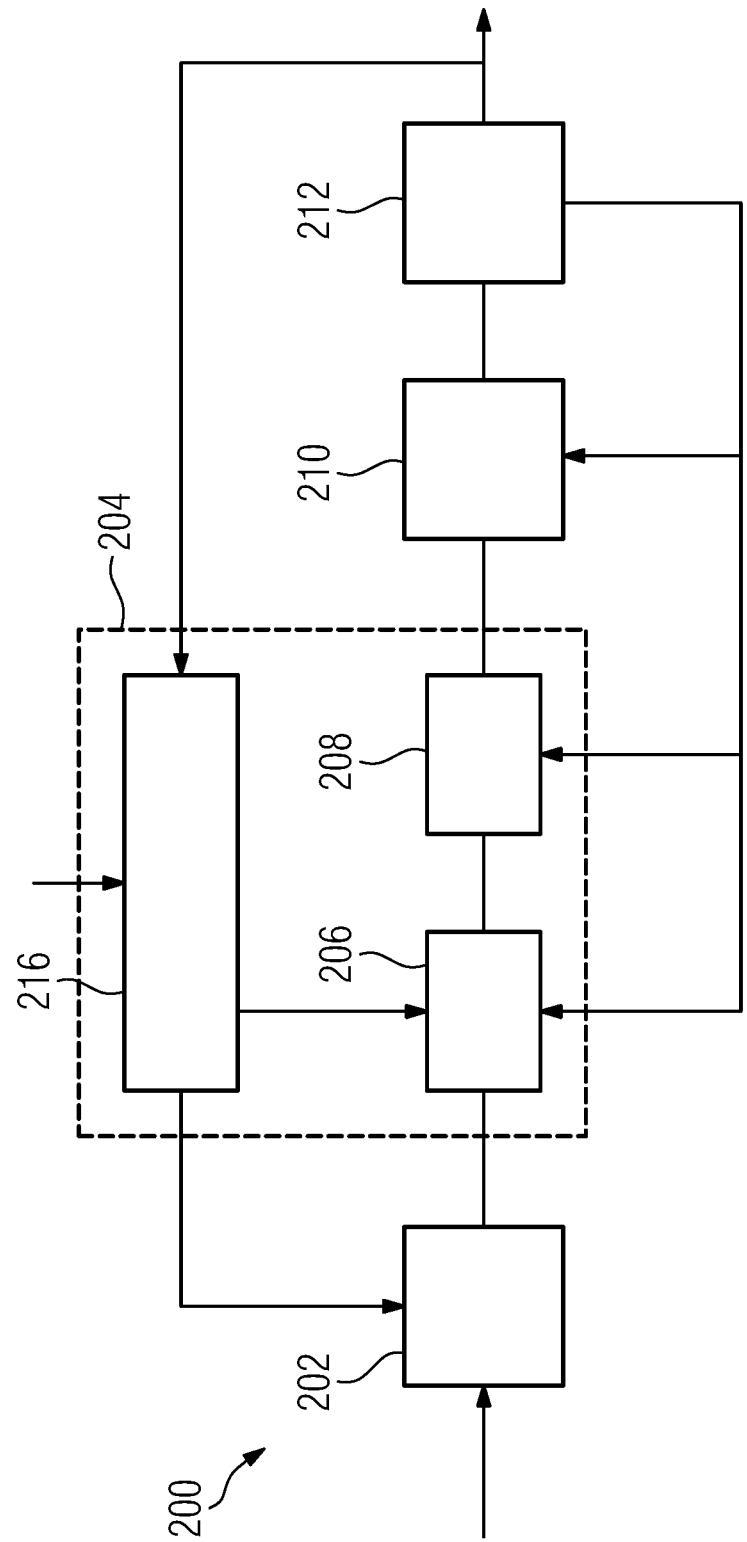
FIG. 2 is a schematic block diagram of a further embodiment of a positioning assistance device with additional misplaced-catheter handling.

FIG. 2 shows a further embodiment of a positioning assistance device 200 with additional misplaced-catheter handling. The structure and operation of the positioning assistance device 200 are quite similar to the embodiment of FIG. 1. The following description therefore focuses on additional and distinguishing features. Otherwise, reference is made to the description FIG. 1. To allow an easier comparison, the three-digit reference labels of corresponding units in the embodiments of FIGS. 1 and 2 have identical last two digits and differ only in the first digit, which is "2" in FIG. 2 and "1" in FIG. 1.

The catheter pre-selection unit 204 of the positioning assistance device 200 additionally comprises an image evaluation unit 216, which is configured to receive three-dimensional image data of the target volume to be exposed to the radiation including one or more catheters currently inserted into the target volume. The catheter image evaluation unit is configured to determine the catheter data of the catheters currently inserted from the image data. The image data is provided in registered form with respect to the common coordinate system mentioned earlier. If not, the image evaluation unit 216 is configured to perform the registration using methods known per se. The position data of the catheters currently inserted can be determined using known pattern recognition solutions applied to contrast features of the catheters showing in the image data. The catheter position determination can be made particularly easy and accurate by using marker features placed at predetermined positions on the inserted catheters and showing as contrast features in the image data.

The image evaluation unit 216 compares the inserted catheter position data thus determined with previously determined target catheter position provided as the positioning assistance output by the positioning assistance control unit 212. Upon detecting a misplaced catheter already inserted into the target volume by detecting a difference between the inserted catheter position data determined from the image data and the associated target catheter position data previously provided for this catheter as an output by the positioning assistance control unit 212, the image evaluation unit adds the misplaced catheter to the candidate catheters to be provided by the candidate catheter providing unit 202.

The positioning assistance control unit 212 is additionally configured to determine and provide adapted dwelling position information and adapted dwelling-time information for the misplaced catheter.

Otherwise, the structure and operation of the positioning assistance device 200 resembles that of the positioning assistance device 100 of FIG. 1.

Figure 3:
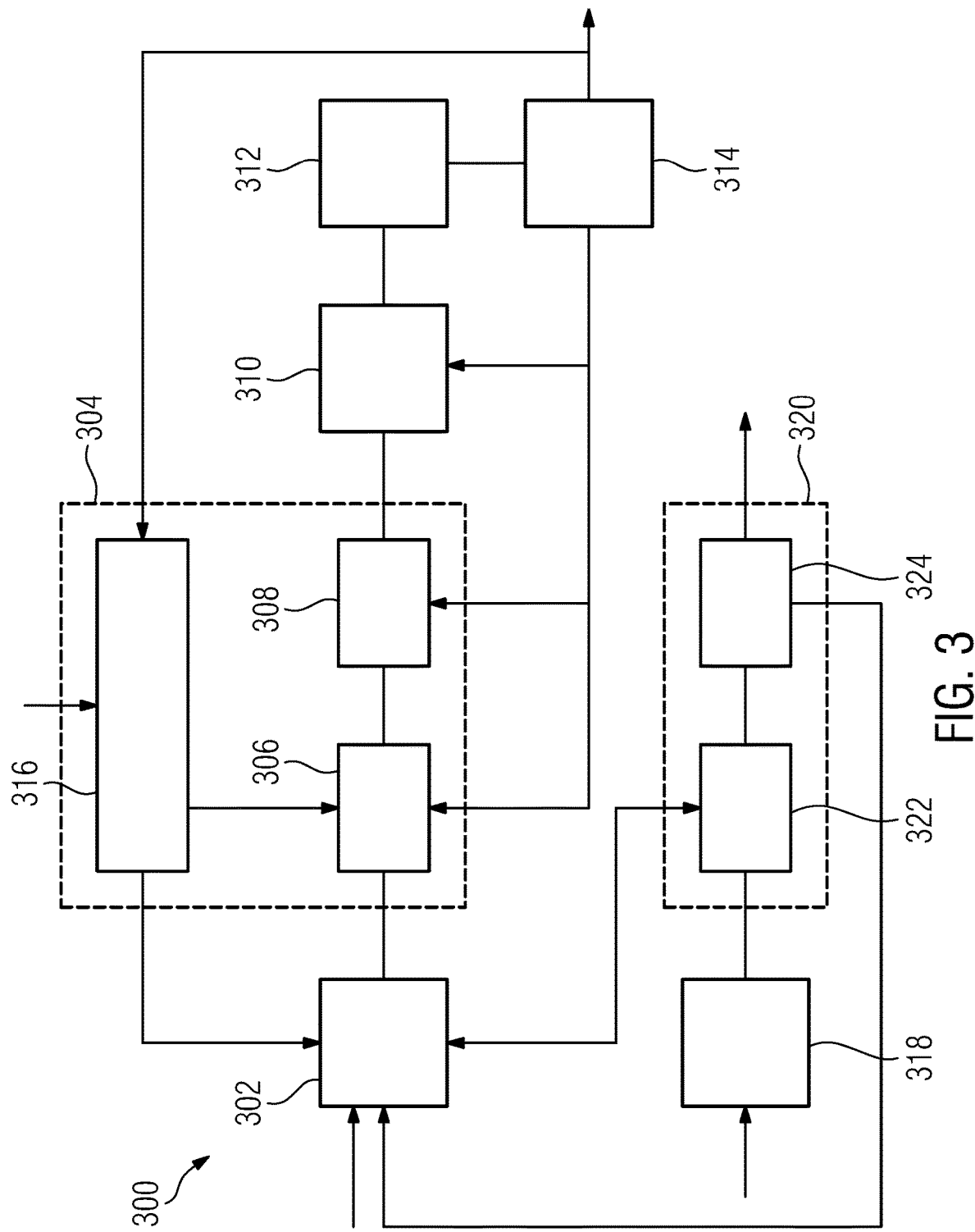
FIG. 3 is a schematic block diagram of a further embodiment of a positioning assistance device with additional misplaced-catheter handling and insertion point positioning assistance.

FIG. 3 is a schematic block diagram of a further embodiment of a positioning assistance device 300 with misplaced-catheter handling (as in the embodiment of FIG. 2) and additional insertion point positioning assistance. The structure and operation of the positioning assistance device 300 are quite similar to the embodiment of FIG. 2. The following description therefore focuses on additional and distinguishing features. Otherwise, reference is made to the description of FIGS. 1 and 2. To allow an easier comparison, the three-digit reference labels of corresponding units in the embodiments of FIGS. 2 and 3 have identical last two digits and differ only in the first digit, which is "2" in FIGS. 2 and "3" in FIG. 3.

The positioning assistance device 300 further provides positioning guidance in the selection of an insertion point.

A candidate insertion point providing unit 318 is configured to provide candidate insertion point data associated with the given target volume and defining candidate insertion points by a respective candidate insertion point position with respect to the common coordinate system (assuming here, for simplicity, a fixed patient position). The provision of the candidate insertion points by the candidate insertion point providing unit 318 is in a simple implementation based on an initial user input of an initial candidate insertion position and adds a set of regularly spaced grid points of further candidate insertion points around the initial candidate insertion position. In another implementation, the candidate insertion point providing unit 318 is configured to receive the three-dimensional image data of the target volume to be exposed to the radiation, which image data is also provided to the catheter pre-selection unit 304 of the positioning assistance device 300. It then determines a two-dimensional axial projection of the target volume onto a predetermined projection plane positioned, with respect to the patient, on the skin or inside the patient. The candidate insertion point providing unit 318 then determines a geometrical center of mass of the axial projection of the target volume. It then determines the candidate insertion points as grid points of a pre-determined two-dimensional grid having the center of mass as a center point.

An insertion point selection unit 320 as a gradient weight determining unit 322 that is configured to receive the set of candidate insertion points and to request and receive, for each of the candidate insertion points, a respective set of candidate catheters from the candidate catheter providing unit 302. The gradient weight determining unit 322 ascertains and provides for each candidate insertion point a sum over all candidate catheters of the gradients with respect to dwelling time of the composite constraint functions, using the candidate insertion point data and the candidate catheter data. Thus, for a given candidate insertion point r, a gradient cumulative weight $g_r$ is calculated by the gradient weight determining unit 322. The gradient cumulative weight $g_r$ represents the sum of the only negative dose-based functional gradients with respect to all dwelling times of all catheters passing via the r-th insertion point:

$$g_r = \Sigma_{c=1}^{N_{cat}^r} g_c. \tag{5}$$

Here, r and c represent the indices of the current candidate insertion point and current candidate catheter, respectively. $N_{cat}^r$ is the total number of candidate catheters spilling out from the candidate insertion point r. $g_c$ has been defined earlier within this specification in equations (1) and (3). For assisting in positioning a next insertion point in addition to any given one, is the above-mentioned equation (3) for $g_c$ is applicable that includes the dose for the given insertion point(s) already in use.

The determined values of $g_r$ for all candidate insertion points are provided to an insertion point selection control unit 324, which is configured to select that candidate insertion point r* corresponding to the most negative gradient value $g_r$ and provide to the operator as well as to the candidate catheter providing unit 02:

$$r^* = \min\{g_r\}, r=1, \ldots, N_r. \tag{6}$$

Otherwise, the structure and operation of the positioning assistance device 300 resembles that of the positioning assistance device 200 of FIG. 2.

Figure 4:
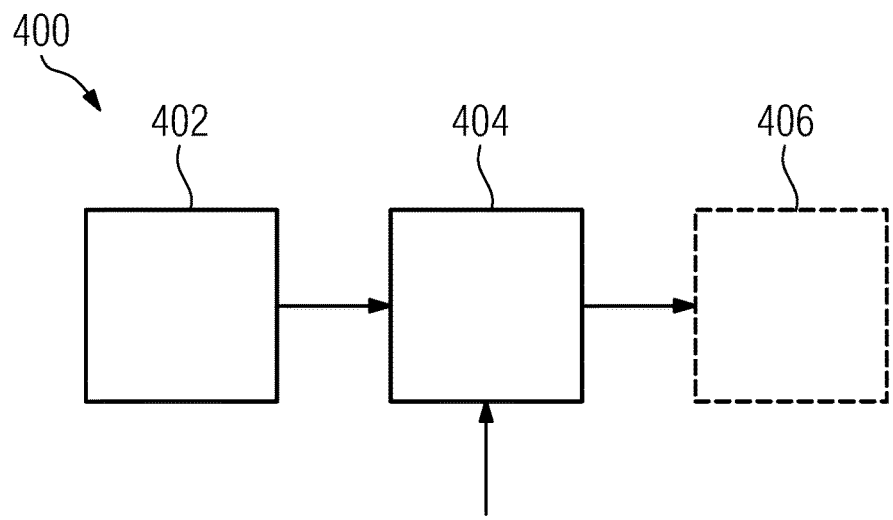
FIG. 4 is a schematic block diagram of a focal radiation therapy arrangement including a positioning assistance device.

FIG. 4 is a schematic block diagram of a focal radiation therapy arrangement 400 according to an embodiment of the present invention. The focal radiation therapy arrangement 400 comprises an imaging device 402 configured to provide three-dimensional image data of a target volume to be exposed to the radiation and of one or more catheters currently inserted into the target volume. The imaging device 402 is suitably a magnetic resonance imaging device or an ultrasound imaging device, or a device combining both mentioned imaging modalities. The focal radiation therapy arrangement 400 further comprises a catheter positioning assistance device 404 according one of the embodiments previously described in the context of the description of FIG. 2 or 3. The catheter positioning assistance device 404 is configured to receive the image data and to provide the next target catheter position in a form registered with respect to the image data.

Optionally, the focal radiation therapy arrangement 400 further comprises a catheter insertion robot, which is configured to receive the target insertion point and the target catheter position from the positioning assistance device, and to insert a catheter into a subject using the received target insertion point and the target catheter position.

Thus, positioning assistance can be provided to a human expert with respect to the positioning of a catheter insertion point (using the embodiment of FIG. 3) and for selecting and positioning the individual catheters using a given insertion point in free-hand operation, or to a robotic arm. In case the expert does not wish positioning assistance with respect to the insertion point, the embodiment of FIG. 2 can be used. At each selected 3D insertion point, the iterative approach described earlier is used to assist in positioning the best set of catheters. A maximum number of catheters to deliver via each insertion point could be set by the user via a suitable GUI.

New implanted catheters are continuously tracked by their 3-D position in real-time using the imaging device 02. As described in the context of the embodiment of FIG. 2, in the case of detected catheter misplacements with respect to planned positions, these tracked misplacements can be taken into account to adaptively re-optimize the remaining set of catheters and corresponding dwell times in order to re-establish dose accuracy, homogeneity and conformality.

The proposed positioning assistance can thus be applied to optimize grid-less free-hand and/or MR-based adaptive focal therapy. Large efficiency gains, e.g., in terms of optimal insertion points and optimal number of selected catheters, adaptive delivered dose correction, real-time orientation guidance, real-time interaction and robust quality control on the clinical focal therapy planning process are achieved. The application field covers brachytherapy, in particular high dose rate (HDR) brachytherapy and/or thermal ablations procedure.

Figure 5:
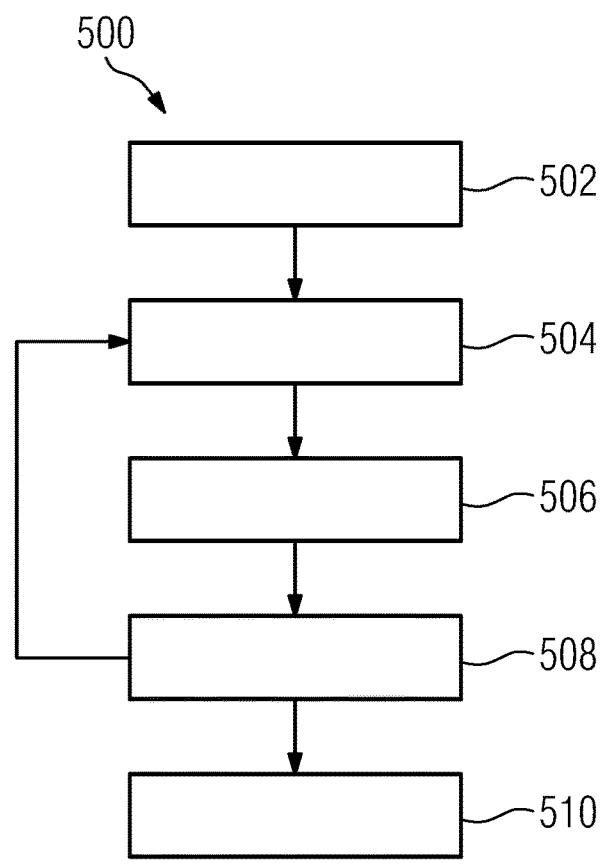
FIG. 5 is a flow diagram of an embodiment of a positioning assistance method for assisting in positioning of catheters in a focal radiation therapy with respect to a pre-determined target volume and a given catheter insertion point.

FIG. 5 is a flow diagram of an embodiment of a positioning assistance method 500 for assisting in positioning of catheters in a focal radiation therapy with respect to a pre-determined target volume and a given catheter insertion point. The flow diagram of FIG. 5 provides an overview of the method, which comprises a candidate catheter providing stage 502, in which candidate catheter data associated with the given catheter insertion point and defining candidate catheters by a respective candidate inserted-catheter position, respective candidate dwelling positions of radiation sources inside a given candidate catheter, and respective associated candidate dwelling times are provided.

Figure 6:
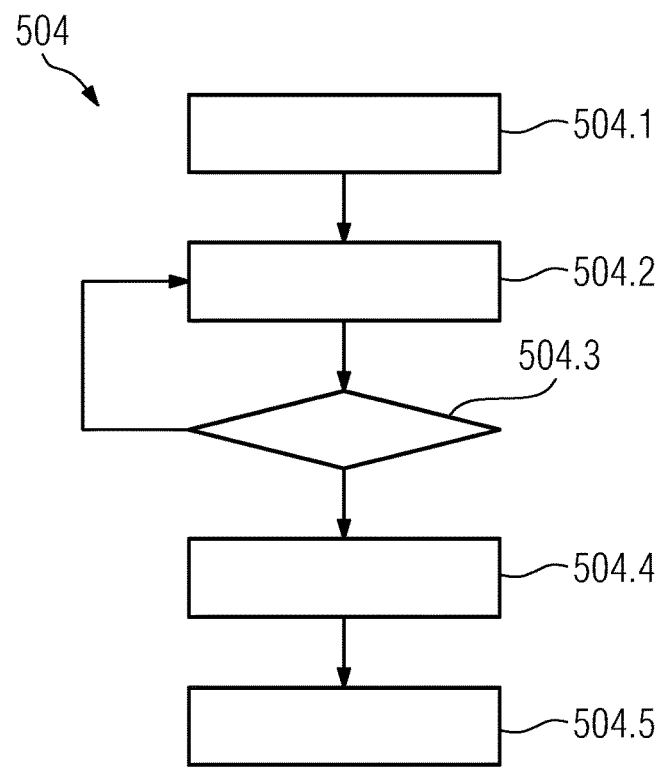
FIG. 6 is a flow diagram showing more detail of step 504 in the method of
FIG. 5.

In a subsequent catheter pre-selection stage 504 a predetermined number of one or more candidate catheters from the candidate catheters is pre-selected. The selection is based on finding the candidate catheter with a steepest descent value of a gradient with respect to dwelling time of a composite constraint function for each current candidate catheter. Additional detail of the process steps preformed in the pre-selection stage 504 will be described in the following with reference to FIG. 6, which is a flow diagram showing more detail of step 504 in the method of FIG. 5. In performing the catheter pre-selection stage 504, the candidate catheter data for a given insertion point are received in a step 504.1 from the candidate catheter providing stage 502. This data comprises the current candidate dwelling times at associated current candidate dwelling positions of the respective candidate catheter. Using this data and a composite constraint function combining at least two linear constraints representing clinical objectives with respect to radiation dose governing the focal radiation therapy, the gradient $g_c$ is determined (definition cf. hereinabove) for a given candidate catheter in step 504.2. In step 504.3 it is checked whether all the gradient $g_c$ has been determined for all candidate catheters received in step 504.1. If that is not the case, step 504.2 is repeated with the next candidate catheter data. After all gradients $g_c$ have been determined, that candidate catheter or a predetermined number of candidate catheters from the set of candidate catheters are identified in step 504.4, which are associated with a steepest descent value of the gradient among the candidate catheters, i.e., with a negative value of $g_c$ having the highest amount. The candidate catheter thus identified data is output to a subsequent dwelling-time pre-selection stage 506 in a step 504.5.

In the dwelling-time pre-selection stage 506, using the current pre-selected candidate catheters provided by the pre-selection stage 504, those current candidate dwelling times for the respective candidate dwelling positions are ascertained and pre-selected, which achieve a minimum of a scalar composite constraint function of dwelling time combining the at least two linear constraints. The scalar composite constraint function is in the present embodiment defined as (equation (2)):

$$F(t) = \sum_{i=1}^{m} w_i f_i(t).$$

All symbols of this function have been defined earlier within the present specification.

Figure 7:
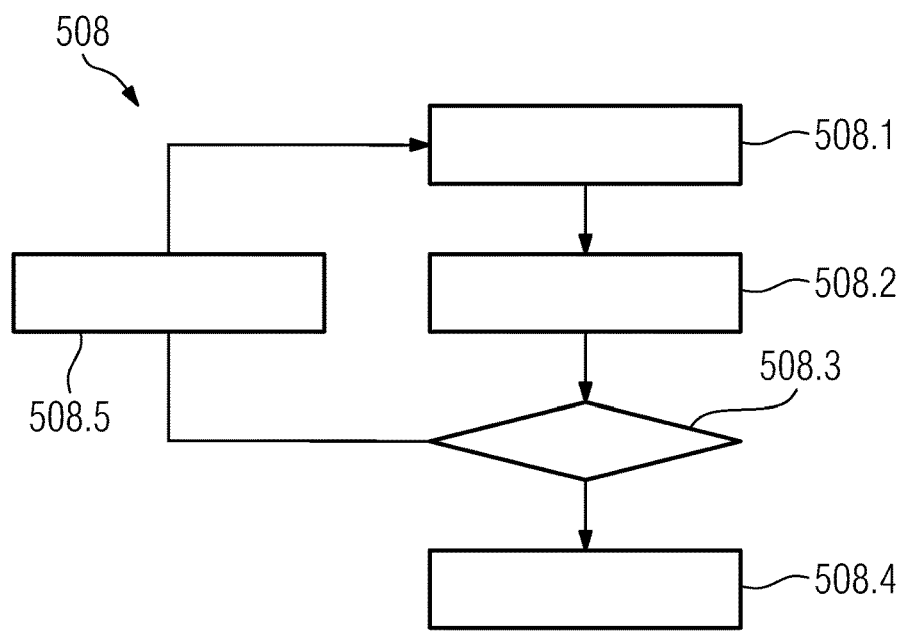
FIG. 7 is a flow diagram showing more detail of step 508 in the method of FIG. 5.

A positioning assistance controlling stage 508 is additionally performed, comprising alternatingly driving operation of the catheter pre-selection stage and the dwelling-time pre-selection stage over a plurality of iteration cycles until detecting that in a current iteration cycle the catheter pre-selection unit has provided a non-negative value of the gradient of the composite constraint function for at least one of the candidate catheters. If that is the case, an output indicative of a next target catheter position as that of the at least one current pre-selected candidate catheter is provided in a subsequent step 510. Further detail of the positioning assistance controlling stage 508 of the method 500 will be described with reference to FIG. 7 below.

The positioning assistance controlling stage 508 comprises receiving, in a step 508.1, the pre-selected candidate catheter data provided by the catheter pre-selection stage 504, and the pre-selected dwelling time values provided by the dwelling-time pre-selection stage 506. Subsequently, the gradient $g_c$ of the composite constraint function are determined for the given set of pre-selected dwelling times in a step 508.2.

It is then determined in a step 508.3 whether any of the gradient values $g_c$ of the composite constraint function for the candidate catheters exhibits a non-negative value. If that is not the case, the method branches to a step 508.5, in which a new iteration cycle of performing the catheter pre-selection stage 504 and the dwelling time pre-selection stage is triggered, followed by performing step 508.1 again to receive the pre-selected candidate catheter data and candidate dwelling times after the triggered iteration cycle has been performed.

When it is determined in a step 508.3 that at least one of the gradient values $g_c$ of the composite constraint function for the candidate catheters exhibits a non-negative value, the associated candidate catheter data is selected in step 508.4 for output as positioning assistance information.

In summary, an efficient direct parameter optimization (DPO) approach is provided, in which a dosimetry gradient-based iterative greedy technique is applied to determine positioning assistance information for catheter insertion in focal radiation therapy, by toggling between optimization of candidate catheter positions and radiation source dwelling times. In the specific case of free hand delivered catheters, the insertion point may be directly selected by the human expert. Using monitoring of the catheter position by additional imaging modalities such as magnetic resonance imaging or ultrasound imaging, the method enables real-time orientation guidance and adaptive dose correction in the course of treatment delivery.

In some embodiments described, potential real-time tracked misplacements can be taken into account to adaptively re-optimize the remaining set of catheters and corresponding dwelling times in order to re-establish optimal dose accuracy, homogeneity and conformality.

The provided devices and methods can be applied to focal radiation therapy, such as high intensity focused ultrasound (HIFU) ablation, radio frequency (RF) ablation, microwave ablation, laser ablation or High Dose Rate (HDR) brachytherapy.

The invention claimed is:

1. A positioning assistance method for assisting in positioning of catheters in a focal radiation therapy with respect to a pre-determined target volume and a given catheter insertion point, the positioning assistance method comprising:

a candidate catheter providing stage, comprising providing candidate catheter data associated with the given catheter insertion point and defining candidate catheters by a respective candidate inserted-catheter position, respective candidate dwelling positions of radiation sources inside a given candidate catheter, and respective associated candidate dwelling times;

a catheter pre-selection stage, comprising
  ascertaining and providing a gradient with respect to dwelling time of a composite constraint function for each current candidate catheter, using current candidate dwelling times at associated current candidate dwelling positions of the each current candidate catheter, the composite constraint function combining at least two linear constraints representing clinical objectives with respect to radiation dose governing the focal radiation therapy; and
  pre-selecting a predetermined number of one or more candidate catheters from the each current candidate catheters, which are associated with a steepest descent value of the gradient among the each current candidate catheters;
a dwelling-time pre-selection stage, comprising
  ascertaining and pre-selecting, using the pre-selected, pre-determined number of the one or more candidate catheters, those current candidate dwelling times for the respective candidate dwelling positions, which achieve a minimum of a scalar composite constraint function of dwelling time combining the at least two linear constraints;
a positioning assistance controlling stage, comprising alternatingly driving operation of the catheter pre-selection stage and the dwelling-time pre-selection stage over a plurality of iteration cycles, and providing, upon detecting that in a current iteration cycle the catheter pre-selection unit has provided a non-negative value of the gradient of the composite constraint function for at least one of the each current candidate catheters, an output indicative of a next target catheter position as that of at least one of the pre-selected, pre-determined number of the one or more candidate catheter catheters.

2. A non-transitory computer readable medium comprising a computer program comprising executable code stored thereon, wherein the executable code is configured for executing the method of claim 1 when executed by a processor of a computer.

3. The method of claim 1, wherein the catheter pre-selection stage further comprises:
  receiving inserted catheter data, which is associated with all catheters already inserted into the target volume and which is indicative of respective inserted-catheter positions, respective dwelling positions of radiation sources, and respective dwelling times associated with the dwelling positions of the catheters already inserted;
  determining a current radiation dose value associated with the dwelling positions and dwelling times associated with the catheters already inserted; and
  determining, for the given candidate catheter, the gradient of the composite constraint function additionally using the current radiation dose value associated with the catheters already inserted.

4. The method of claim 3, wherein the catheter pre-selection stage further comprises:
  receiving three-dimensional image data of the target volume to be exposed to the radiation sources and of one or more catheters currently inserted into the target volume; and
  determining the candidate catheter data of catheters currently inserted from the image data.

5. The method of claim 4, wherein the catheter pre-selection stage further comprises:
  upon detecting a misplaced catheter already inserted into the target volume by detecting a difference between catheter position data determined from the image data and an associated target catheter position previously provided for this catheter as an output by the positioning assistance controlling stage, adding the misplaced catheter to the candidate catheters; and wherein
  the positioning assistance controlling stage further comprises determining and providing adapted dwelling position information and adapted dwelling-time information for the misplaced catheter.

6. The method of claim 3, wherein, in case at least one catheter is already inserted,
  the candidate pre-selection stage further comprises determining for the given candidate catheter, the gradient of the composite constraint function additionally using the current radiation dose value associated with the catheters already inserted as $$g_c = \sum_{j=1}^{N_c^t} \begin{cases} \dfrac{\partial F(M_0 t_0 + M_1 t_1 + \ldots + M_n t_n)}{\partial t_{c,j}}, & \text{if} \\ \dfrac{\partial F(M_0 t_0 + M_1 t_1 + \ldots + M_n t_n)}{\partial t_{c,j}} < 0 \\ 0, & \text{otherwise,} \end{cases}$$

$$c = 1, \ldots, N_{cat}^{r^*}.$$

wherein
$M_0, M_1, \ldots M_n$ are dose rate influence matrices of catheters of index n=0,1 . . . n which are already inserted,
$t_0, t_1, \ldots, t_n$ are dwelling times associated with the catheters of index n=0,1, n which are already inserted; and wherein
the dwelling-time pre-selection stage further comprises ascertaining the current candidate dwelling times for the respective candidate dwelling positions, which achieve a minimum of the scalar composite constraint function $$F(t) = \sum_{i=1}^{m} w_i f_i(t) = \sum_{i=1}^{m} w_i f_i(M_0 t_0 + M_1 t_1 + \ldots + M_n t_n).$$

7. The method of claim 1, wherein the catheter pre-selection stage further comprises:
  calculating the gradient $g_c$ with respect to dwelling time of the composite constraint function for each current candidate catheter as:

$$g_c = \sum_{j=1}^{N_c^t} \begin{cases} \dfrac{\partial F(t)}{\partial t_{c,j}}, & \text{if } \dfrac{\partial F(t)}{\partial t_{c,j}} < 0 \\ 0, & \text{otherwise} \end{cases}, c = 1, \ldots, N_{cat}^{r^*}.$$

wherein
c is an index identifying a respective catheter,
$N_c^t$ is a total number of dwelling positions for the c-th catheter,
t is a dwelling time vector of dwelling times at dwelling positions,
j an index identifying a respective dwell time position,
$r^*$, is an index identifying a current insertion point,
$N_{cat}^{r^*}$ is the total number of divergent catheters passing the current insertion point, $$F(t) = \sum_{i=1}^{m} w_i f_i(t),$$

i is an index identifying a respective linear constraint,
m is a total number of linear constraints,
$f_i(t)$ is a set of linear constraints representing clinical objectives given as functions of dwelling times t of a respective radiation source in the given candidate catheter, and
$w_i$ are weighting factors indicative of a priority of a given linear constraint; and wherein the dwelling-time pre-selection stage comprises ascertaining the current candidate dwelling times for the respective candidate dwelling positions, which achieve a minimum of the scalar composite constraint function $$F(t) = \sum_{i=1}^{m} w_i f_i(t),$$

taking into account predetermined upper and lower limits for the current candidate dwelling times.

8. The method of claim 1, further comprising providing candidate insertion point data associated with the pre-determined target volume and defining candidate insertion points by a respective candidate insertion point position;
  requesting and receiving, for each candidate insertion point, a respective set of candidate catheters from the candidate catheter providing stage;
    ascertaining and providing for each candidate insertion point a sum over all candidate catheters of the gradient with respect to dwelling time of the composite constraint function, using the candidate insertion point data and the candidate catheter data; and
    selecting as a next insertion point from the candidate insertion points that candidate insertion point, which among the candidate insertion points is associated with the steepest descent value of the sum over all candidate catheters of the gradients.

9. The method of claim 8, further comprising:
receiving three-dimensional image data of the target volume to be exposed to the radiation sources;
determining a two-dimensional axial projection of the target volume onto a predetermined projection plane on or in a subject;
determining a geometrical center of mass of the axial projection of the target volume; and
determining the candidate insertion points as grid points of a pre-determined two-dimensional grid having the center of mass as a center point.

10. The method of claim 1, further comprising:
receiving, from an imaging device, three-dimensional image data of the target volume to be exposed to the radiation sources and of one or more catheters currently inserted into the target volume, wherein the method further comprises receiving the image data and providing the next target catheter position in a form registered with respect to the image data.

11. The method of claim 10, further comprising providing a target insertion point and a target catheter position to a catheter insertion robot, which is configured to insert a catheter into a subject using the received target insertion point and the target catheter position.

\* \* \* \* \*